US00PP15475P2

(12) United States Plant Patent
Valstar

(10) Patent No.: US PP15,475 P2
(45) Date of Patent: Jan. 11, 2005

(54) ***STROMANTHE* PLANT NAMED 'VALMIC'**

(50) Latin Name: *Stromanthe sanguinea*
Varietal Denomination: Valmic

(75) Inventor: Oscar R. Valstar, Maasland (NL)

(73) Assignee: Handelskwekerij Gebr. Valstar C.V., Maasland (NL)

( * ) Notice: Subject to any disclaimer, the term of this patent is extended or adjusted under 35 U.S.C. 154(b) by 0 days.

(21) Appl. No.: 10/766,770

(22) Filed: Jan. 28, 2004

(51) Int. Cl.[7] ..... A01H 5/00
(52) U.S. Cl. ..... Plt./373
(58) Field of Search ..... Plt./373

*Primary Examiner*—Kent Bell
(74) *Attorney, Agent, or Firm*—C. A. Whealy

(57) ABSTRACT

A new and distinct cultivar of *Stromanthe* plant named 'Valmic', characterized by its upright and outwardly spreading plant habit; freely basally clumping growth habit; and large green and creamy white-colored leaves with purple-colored lower surfaces.

1 Drawing Sheet

Botanical classification/cultivar designation: *Stromanthe sanguinea* cultivar Valmic.

BACKGROUND OF THE INVENTION

The present Invention relates to a new and distinct cultivar of *Stromanthe* plant, botanically known as *Stromanthe sanguinea,* and hereinafter referred to by the name 'Valmic'.

The new *Stromanthe* was discovered by the Inventor in a controlled environment in Honselersdijk, The Nertherlands in 1999, as a naturally-occurring whole plant mutation of *Stromanthe sanguinea* cultivar Stripestar, not patented. The new *Stromanthe* was observed as a single flowering plant within a population of plants of the cultivar Stripestar. The selection of this plant was based on its unique foliage coloration.

Asexual reproduction of the new *Stromanthe* by divisions in a controlled environment in Honselersdijk, The Netherlands since 1999 has shown that the unique features of this new *Stromanthe* are stable and reproduced true to type in successive generations.

SUMMARY OF THE INVENTION

The cultivar 'Valmic' has not been observed under all possible environmental conditions. The phenotype may vary somewhat with variations in environment such as temperature and light intensity, without, however, any variance in genotype.

The following traits have been repeatedly observed and are determined to be the unique characteristics of 'Valmic'. These characteristics in combination distinguish 'Valmic' as a new and distinct *Stromanthe* cultivar:

1. Upright and outwardly spreading plant habit.
2. Freely basally clumping growth habit.
3. Large green and creamy white-colored leaves with purple-colored lower surfaces.

Plants of the new *Stromanthe* are most similar to plants of the parent cultivar Stripestar; however plants of the new *Stromanthe* differ from plants of the cultivar Stripestar primarily in leaf coloration as leaves of plants of the cultivar Stripestar are solid green in color with greyed green-colored midveins.

BRIEF DESCRIPTION OF THE PHOTOGRAPHS

The accompanying colored photographs illustrate the overall appearance of the new *Stromanthe,* showing the colors as true as it is reasonably possible to obtain in colored reproductions of this type. Colors in the photographs may differ slightly from the color values cited in the detailed botanical description which accurately describe the colors of the new *Stromanthe.*

The photograph at the top of the sheet comprises a side perspective view of a typical plant of 'Valmic' grown in a container.

The photograph at the bottom of the sheet is a close-up view of typical leaves of 'Valmic'.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants grown in Maasland, The Netherlands, under commercial practice during the winter in a glass-covered greenhouse. During the production of the plants, day temperatures were about 22° C. and night temperatures were about 20° C. Plants were grown with one plant per 17-cm container. Plants were about 20 weeks old when the photographs and description were taken.

Botanical classification: *Stromanthe sanguinea* cultivar Valmic.

Parentage: Naturally-occurring whole plant mutation of *Stromanthe sanguinea* cultivar Stripestar, not patented.

Propagation:

*Type.*—By divisions.

*Root description.*—Dense, freely branching and white in color.

Plant description:

*Plant form.*—Upright and outwardly spreading plant habit; broadly inverted triangle; freely basally clumping growth habit, about nine clumps per plant; bushy and moderately vigorous growth habit.

*Plant height.*—About 80 cm.

*Plant width.*—About 105 cm.

*Leaves.*—Arrangement: Alternate, single. Quantity per clump: About seven. Length: About 42.9 cm. Width: About 9.8 cm. Shape: Narrowly lanceolate. Apex: Apiculate. Base: Obtuse to truncate. Margin: Entire. Texture, upper and lower surfaces: Glabrous, smooth; leathery; lateral veins prominent on upper surface. Venation pattern: Pinnate. Color: Developing leaves, upper surface: 147A with random spots, streaks and blotches, 147D to 158A to 158B. Developing leaves, lower surface: N186C to 187A with random spots, streaks and blotches, 185B. Fully expanded leaves, upper surface: Between 136A and 139A with random spots, streaks and blotches, 148D to 158A to 158B. Fully expanded leaves, lower surface: N186C to 187A with random spots, streaks and blotches, 185B. Venation, upper surface: Midvein, 143A; lateral veins same as lamina. Venation, lower surface: Midvein, 183A; lateral veins, N186A. Petiole: Length: About 44.6 cm. Diameter: About 5.5 mm. Color: Between 152A and N199C. Geniculum length: About 3.6 mm. Geniculum width: About 5 mm. Geniculum color: Between 152A and N199C. Wing length: About 25.9 cm. Wing width: About 6 mm. Wing color, upper and lower surfaces: 182B to 182C.

Flower description: Flower development has not been observed on plants of the new *Stromanthe*.

Disease/pest resistance: Plants of the new *Stromanthe* have not been observed to be resistant to pathogens and pests common to *Stromanthe*.

Temperature tolerance: Plants of the new *Stromanthe* have been observed to tolerate temperatures from 15 to 30° C.

It is claimed:

1. A new and distinct cultivar of *Stromanthe* plant named 'Valmic', as illustrated and described.

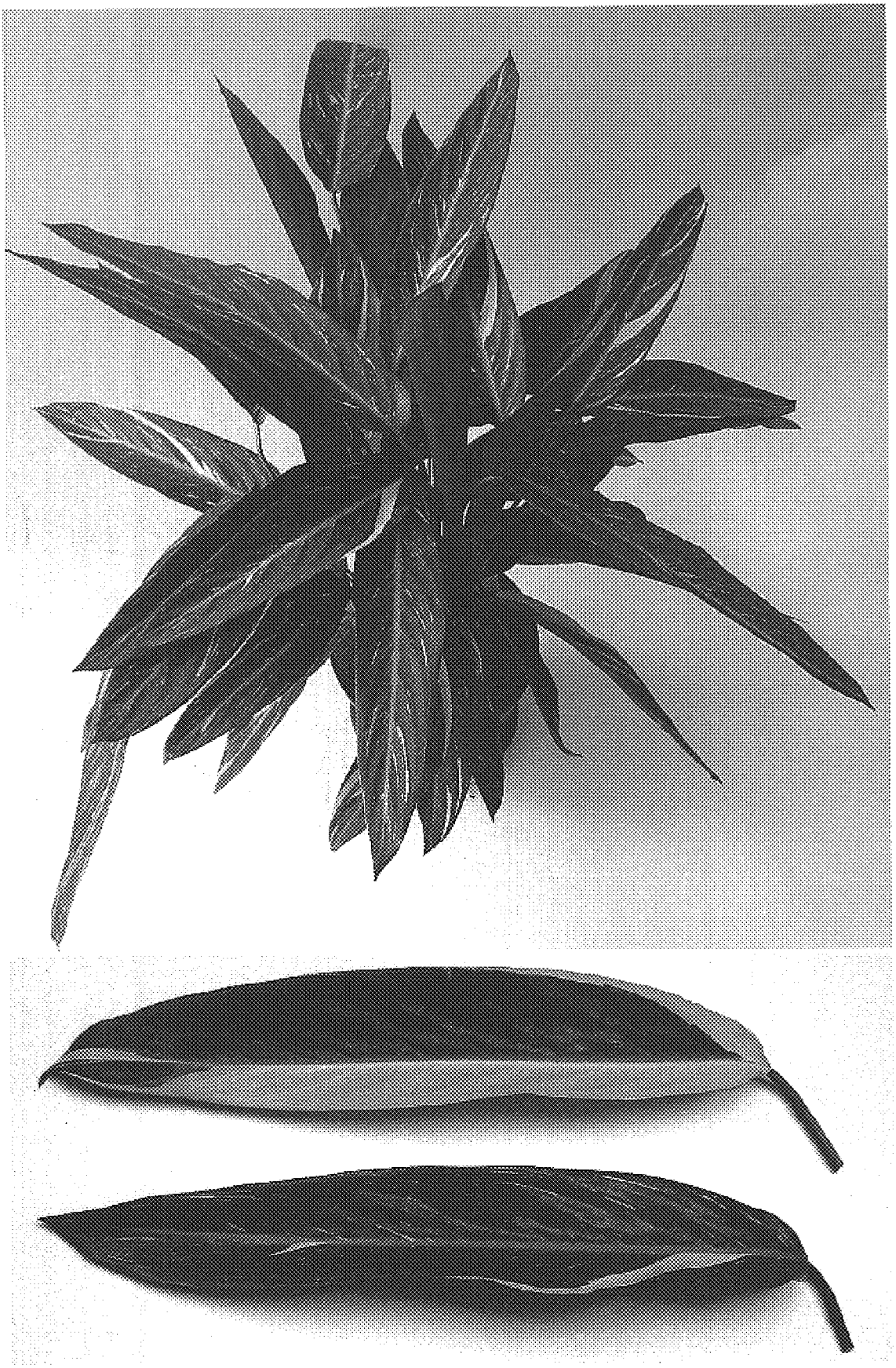

* * * * *